United States Patent [19]

Riedel

[11] Patent Number: 4,967,740
[45] Date of Patent: Nov. 6, 1990

[54] DISPENSABLE TAPES

[75] Inventor: John E. Riedel, White Bear Lake, Minn.

[73] Assignee: Minnesota Mining and Manufacturing Company, St. Paul, Minn.

[21] Appl. No.: 405,116

[22] Filed: Sep. 8, 1989

Related U.S. Application Data

[63] Continuation of Ser. No. 872,970, Jun. 11, 1986, abandoned.

[51] Int. Cl.$^5$ .............................................. A61L 15/00
[52] U.S. Cl. ...................................... 128/156; 428/40; 428/288
[58] Field of Search ............... 428/40, 207, 294, 288; 525/58; 128/155, 156

[56] References Cited

U.S. PATENT DOCUMENTS

| Re. 24,906 | 12/1960 | Ulrich | 206/59 |
|---|---|---|---|
| 2,532,011 | 11/1950 | Dahlquist et al. | 525/58 X |
| 3,121,021 | 2/1964 | Copeland | 117/122 |
| 3,265,765 | 8/1966 | Holden et al. | 260/876 |
| 3,318,852 | 5/1967 | Dixon | 260/78.5 |
| 3,389,827 | 6/1968 | Abere et al. | 220/53 |
| 3,967,031 | 6/1976 | Lambert | 428/294 |
| 4,112,213 | 9/1978 | Waldman | 526/279 |
| 4,176,667 | 12/1979 | Herring | 128/156 |
| 4,202,925 | 5/1980 | Dabroski | 128/156 |
| 4,349,020 | 9/1982 | Krikorian | 128/156 |
| 4,366,814 | 1/1983 | Riedel | 128/156 |
| 4,367,732 | 1/1983 | Poulsen | 128/156 |
| 4,381,611 | 5/1983 | Wishman | 128/156 |
| 4,632,857 | 12/1986 | Wolfrey et al. | 428/40 X |
| 4,650,706 | 3/1987 | Emmel | 428/40 |

OTHER PUBLICATIONS

U.S. Pat. application Ser. No. 732,587.

Primary Examiner—Alan W. Cannon
Attorney, Agent, or Firm—Donald M. Sell; Walter N. Kirn; Philip M. Goldman

[57] ABSTRACT

Disclosed are tapes for medical use, prepared in a one-pass coating operation in which an extensible tape backing is treated simultaneously with LAB material and elastomer. The resultant tapes exhibit release characteristics and elasticity that enable them to be dispensed in the form of a linerless rolls or in pads without deformation or loss of adhesion.

17 Claims, 2 Drawing Sheets

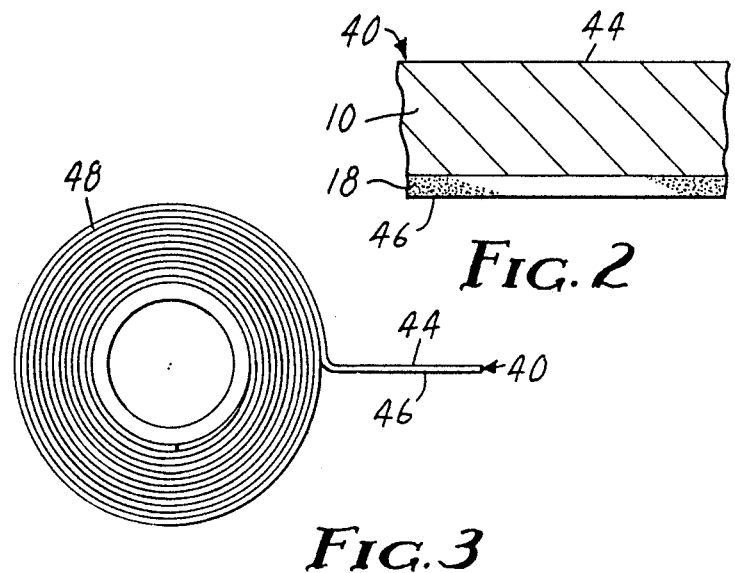
Fig. 2
Fig. 3
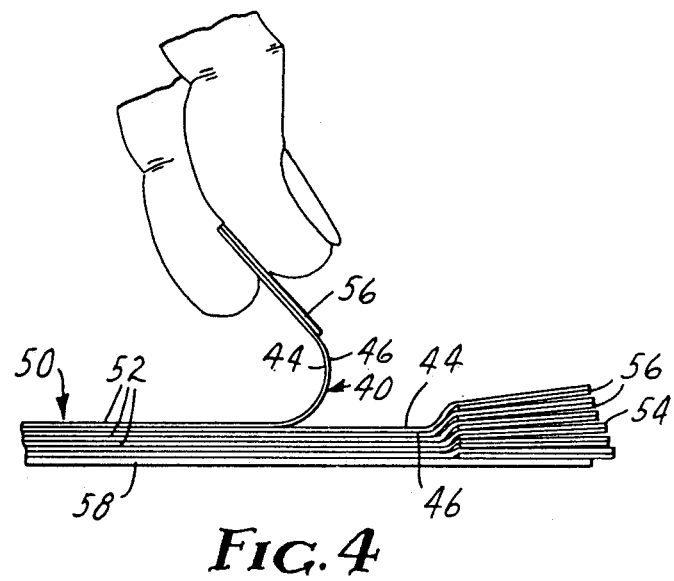
Fig. 4

DISPENSABLE TAPES

This is a continuation of application Ser. No. 872,970, filed June 11, 1986, now abandoned.

TECHNICAL FIELD

This invention relates to processes for making moisture vapor permeable tapes for use on mammalian skin. In another aspect, this invention relates to the tapes themselves, and to the dispensation of such tapes in the form of linerless rolls or in pads.

BACKGROUND ART

Contemporary moisture vapor permeable tapes, such as medical tapes, frequently involve the combination of two principal layers—a "breathable" backing layer, and an adhesive layer, generally a pressure-sensitive adhesive, useful for applying that backing layer to the skin.

A number of conventional medical tapes have relatively rigid backings, and are therefore amenable to being dispensed in the form of linerless rolls or in pads, e.g., as disclosed in (co-pending U.S. application Ser. No. 732,587, filed May 10, 1985). The tape in such a roll or pad is typically made up of a backing layer, a pressure-sensitive adhesive layer and optionally, if necessary, a low adhesion backsize ("LAB") material applied to the backing of the tape, i.e., on the side opposite that bearing adhesive, to allow the roll to be easily unwound, or to facilitate the separation of one pad sheet from another.

The use of LAB materials to improve the release characteristics, i.e., increase the ease of separation, of tapes has been described previously, e.g., in U.S. Pat. Nos. 2,532,011 and 3,318,852. LAB's have been applied to backings as the only coating in a one-pass coating operation, e.g., as described in the '011 patent. LAB's have also been applied as the second coating of a two-pass coating operation, e.g., wherein a fibrous backing is first coated with another material such as a fiber-binding and/or filling material which is then dried and followed by an LAB material applied as a second coating, e.g., as disclosed in the '011 patent as well as in U.S. Pat. No. 3,121,021.

The use of an LAB material in a blend with a compatible or an incompatible "non-tacky high polymer" are mentioned in '011 patent as expedient means of lowering the amount of LAB needed, thereby lessening the cost of its use.

In contrast to the above-described tapes having relatively rigid backings, there are a variety of tapes that have not to date been dispensable in the form of linerless rolls or in pads in a manner that does not compromise desirable inherent properties of the backing. Such tapes typically have fabric backings that exhibit a variety of desirable properties for medical use, such as softness and conformability, as well as moisture vapor permeability. Such fabrics are generally easily extensible as well, in that they can be extended in length or width by tension. Unfortunately however, such fabrics are also typically inelastic, i.e., exhibit little or no retractive forces when extended. As a result, the fabrics will not return to their original shape when the tension is released.

U.S. Pat. No. 4,366,814 describes the impregnation of such extensible backings with elastomers in order to impart elasticity to the backings, thereby allowing the use of the resultant backings, e.g., as stretch bandages and as backings for adhesive tapes. The tapes made from extensible fabrics that have been impregnated with elastomer must frequently be dispensed using liners however, since the backings are still generally deformable by the forces that would be required to pull them from a linerless roll or pad. The need for a liner, however, adds time, cost and inconvenience to the manufacture and use of such tapes.

The use of an LAB material applied as the second coat in a conventional two-pass coating operation, i.e., after elastomer, may enable such tapes to be dispensed without a liner from a roll or pad, but frequently is accompanied by a compromise of some or all of the very properties for which the backing was chosen such as moisture vapor permeability, softness and/or conformability, or else the backing exhibits insufficient release characteristics and/or elasticity.

As a result, in spite of the drawbacks associated with their use, liners have still been generally preferred for use with many elastomer-impregnated tapes, as opposed to the use of linerless tapes with LAB coatings.

SUMMARY OF THE INVENTION

The tapes of the present invention are made in a one-pass coating operation, in which a compatible combination of low adhesion backsize material and elastomer are simultaneously applied, preferably in the same solution, to treat an extensible backing. Surprisingly, the resultant tapes retain their original properties such as moisture vapor permeability, softness and conformability and also exhibit significantly improved physical properties, particularly improved release characteristics and elasticity, as compared to tapes made by a two-pass coating operation wherein elastomer and LAB are added sequentially with a drying step between. Elasticity of the resultant tape is frequently even improved over that of a tape having a coating of elastomer alone, suggesting an unexpected but welcome complimentary effect of the combination of elastomer and LAB on elasticity as well as on release characteristics.

Furthermore, the ability to produce such tape in a one-pass, as opposed to two-pass, coating operation yields significant benefits in terms of the cost, efficiency and effectiveness of the manufacture of these materials. Most importantly, sufficient release teristics can now be imparted to such tapes, in addition to elasticity, such that the tapes can be now dispensed without deformation or substantial loss of adhesion in the form of a liner-free roll or in a pad, i.e., without the cost and inconvenience of including a liner between contacting layers, and without adverse affect on the desireable properties of the tape's backing.

The present invention provides a method for making dispensable tape comprising the steps of
 (a) treating an extensible backing simultaneously with a compatible combination comprising
  (i) at least one low adhesion backsize material, and
  (ii) at least one elastomer, and
 (b) drying the resultant treated backing to remove substantially all solvent.

The backing can be treated with LAB and elastomer at any time, e.g., before or after it is coated with a pressure sensitive adhesive layer.

The present invention also provides dispensable tapes themselves, as well as rolls and pads for dispensing such tapes.

BRIEF DESCRIPTION OF THE DRAWING

The present invention will be more thoroughly explained with reference to the accompanying drawing where like numbers refer to like parts and wherein:

FIG. 2 shows a sectional view of a portion of a preferred tape of the present invention.

FIG. 3 is a side elevational view of a preferred roll of tape of the present invention.

FIG. 4 is an enlarged elevational view of a preferred tape pad for dispensing tapes of the present invention.

DETAILED DESCRIPTION

Figure 1:
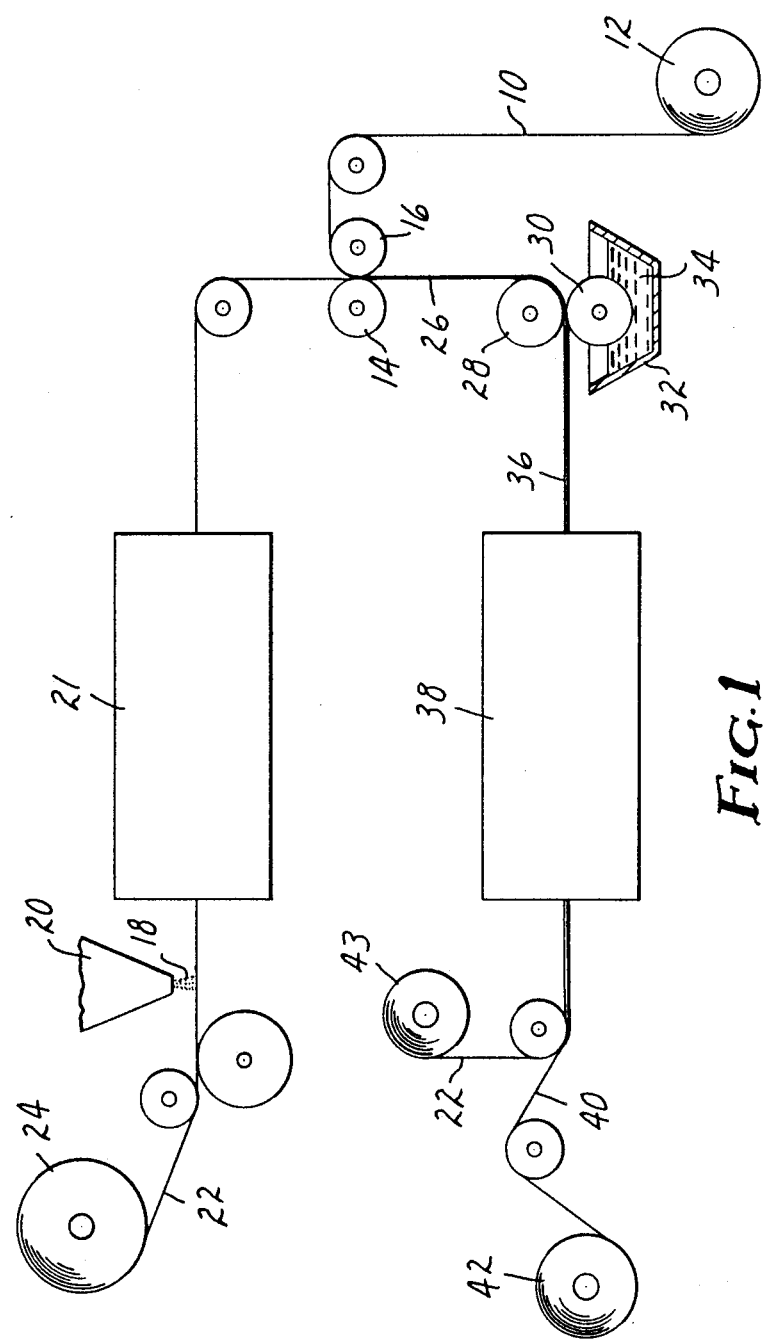
FIG. 1 is a diagram of a preferred method of making the tape material of the present invention.

Backings useful in the practice of the present invention are well known in the art, and generally are fabric backings having normally poor elastic behavior, i.e., those that do not have sufficient elastic recovery to return to their original shape when subjected to tension, such as the normal physical manipulation associated with medical use. These backings however are typically "extensible", i.e., have sufficient "stretch", in that they can be extended in length and/or width by tension, and exhibit "hand" and "drape" characteristics, as these words are commonly defined, that makes them desirable for many medical uses. These backings therefore are those that would benefit, in terms of improved elastic behavior, by impregnation with an elastomer, e.g., as described in U.S. Pat. No. 4,366,814. The elastomer preferably is capable of binding the fibers of the fabric, without filling the holes of the fabric, so that the fabric becomes sufficiently elastic without adverse effect on other desirable properties, such as moisture vapor permeability, softness and conformability. The term "adverse affect" as used herein refers to changes in the inherent properties of a backing or an adhesive coating that would render either unsuitable or undesireable for use in a medical tape.

Suitable backings include, but are not limited to, commercially available fabrics such as nonwoven, woven or knitted fabrics. Such fabrics may be constructed of a wide range of synthetic or natural fibers, used singly or in blends. Examples of suitable backings include nonwoven fabrics such as carded, spun-bonded, spun-laced, air-laid, and stitch-bonded fabrics; woven fabrics having sufficient stretch to benefit from the use of an elastomer; and knitted fabrics, including warp-knitted and weft-knitted fabrics.

Preferred backings exhibit a desired combination of such inherent properties as moisture vapor permeability, softness, comformability, yield modulus, texture, appearance, processability and strength. The particular combination of properties is determined in large part by the application chosen. For example, for many uses as a medical tape, the fabric will typically be soft and conformable, have a low yield modulus, and will be of sufficient strength for the desired application and for dispensation in roll or pad form.

Examples of preferred backings include, but are not limited to, "Sontara", a spun-laced polyester nonwoven fabric available commercially from E. I. DuPont de Nemours & Co., Wilmington, Del.; "Durapore", a square-weave rayon woven fabric available commercially from Burlington Industrial Fabrics Co., Rockleigh, N.J.; "WS-7508350AK", an acetate tricot warp knit fabric available commercially from Gold Mills Inc., New York, N.Y.; and air-laid nonwoven thermally bonded fabrics, such as, the "Webril M" series available commercially from The Kendall Co., Walpole, N.J.

The term "low adhesion backsize" ("LAB") as used herein shall refer to any material capable of treating a tape backing so as to improve the release characteristics of the backing. LAB materials suitable for use are widely known and described, e.g., in U.S. Pat. Nos. 2,532,011 and 3,318,852, the disclosures of which are hereby incorporated by reference. Preferred LAB materials are those that exhibit a desired combination of such properties as: compatibility with the elastomer; solubility or dispersibility in a solvent; release characteristics imparted to the backing; suitability for use on skin; and cost and ease of use.

Examples of preferred LAB materials include, but are not limited to, polyvinyl carbamate compounds and derivatives thereof as described in U.S Pat. No. 2,532,011, and copolymers based on fluorochemical monomers, as described in U.S. Pat. No. 3,318,852. A particularly preferred LAB is polyvinyl N-octadecyl carbamate prepared as described at column 9 of the '011 patent.

As will be readily apparent to those skilled in the art, LAB material is used to treat a backing at a concentration and in a manner that, in combination with elastomer, will impart sufficient release characteristics to the backing, i.e., that will allow a second tape of the same type to removably contact the backing in a manner that does not adversely affect either tape. The LAB treatment preferably will also allow limited adhesive forces to remain between a contacting adhesive and the backing, i.e., forces that are sufficient to hold a roll or pad in its intended form. A preferred LAB treatment will require a peel force that allows easy removal of tape from the roll or pad without causing deformation of the backing or adversely affecting the adhesion of the adhesive surface (e.g., by delamination or by removal of LAB from the contacting backing).

Elastomers suitable for use in the present invention are well known, and described, e.g., in U.S. Pat. Nos. 3,265,765 and 4,366,814, the disclosures of which are hereby incorporated by reference. Examples of suitable elastomers are synthetic rubbers or plastics, which, at room temperature, can be stretched under low stress and, upon immediate release of stress, will return with force to their approximate original length.

Preferred elastomers exhibit a desired combination of such properties as compatibility with the LAB of choice, solubility or dispersability in a solvent, elasticity imparted to the backing, strength, softness, suitability for use on skin, and cost and ease of use.

Examples of preferred elastomers are block copolymers of monovinyl aromatic hydrocarbons and conjugated dienes as described in U.S Pat. No. 3,265,765, polyurethanes, acrylics, acrylic-olefinic copolymers, vinyls and other natural and synthetic rubbers.

Particularly preferred elastomers include, but are not limited to, organic elastomers such as: the "Kraton" series, including "Kraton D-1101" and "D-1107" which are thermoplastic rubbers available commercially from Shell Oil Company, Oak Brook, Ill.; "VYNS" and "VAGH", both being vinyl chloride-vinyl acetate resins, available commercially from Union Carbide Corp., New York, N.Y.; "Elvacite" acrylic resins, available commercially from DuPont, Wilmington, Del.; "Piccolastic D" thermoplastic hydrocarbon resins, available commercially from Hercules, Inc., Wilmington, Del.; "NACRYLIC" type acrylic resins including "X4260" and "X4460", available commercially from National Starch and Chemical Corp., Bridgewater, N.J., and modified aromatic urethane resins such as "QW4391", available commercially from K. J. Quinn & Co., Malden, Mass.

As will be readily apparent to those skilled in the art, elastomer is used to treat a backing at a concentration and in a manner that, in combination with LAB, will impart sufficient elasticity to the backing to enable it to return to substantially its original size and shape when subjected to the normal physical manipulation associated with medical use. Preferably the elastomer will be uniformly impregnated on or within the fibers of the fabric without filling the spaces between fibers.

The particular combinations of LAB and elastomer useful in the present invention are those that are "compatible", i.e., capable of being applied simultaneously, i.e., without the need for a solvent drying step, to treat a backing in a one-pass coating operation. Preferably both LAB and elastomer can be used at workable levels that are economically feasible and that achieve the desired release characteristics and elasticity without adversely effecting the inherent properties of the backing.

Particularly prefered are LAB/elastomer combinations that are able to be distributed throughout the final dried backing in approximately the same ratios in which they were added, i.e., that do not differentially migrate or stratify with respect to each other to an appreciable degree, e.g., with LAB becoming more concentrated on the surface, and elastomer on the interior of the backing.

Indeed, the word "treat" and variations thereof as used herein are intended to refer to any simultaneous application, and resultant physical form or distribution, of LAB and elastomer in or on a backing that is.effective to provide the desired release characteristics and elasticity to the backing. It is believed that the improved properties apparent in the tapes of the present invention are due in large part to a different final distribution of LAB and elastomer in the backing, i.e., a distribution in which both are present in a homogeneous and continuous form throughout the backing, as compared to that expected from a conventional two-pass coated backing. In the latter case, it is expected that LAB would tend to be more concentrated, with respect to elastomer, as well as with respect to the interior of the backing, at the surface of the backing.

As a result, the release characteristics of a two-pass coated backing could be adversely affected, e.g., by the selective chemical extraction of the LAB, under conditions that would not also adversely affect the elasticity imparted by the elastomer. With a backing treated according to the method of the present invention, on the other hand, one would necessarily adversely affect elasticity as well, by the extraction conditions necessary to adversely affect release characteristics.

As used herein the word "solvent" refers to any substantially fluid vehicle (e.g., water, organic solvents); and the words "soluble" and "solution" refer to any physical form of LAB and/or elastomer in a solvent (e.g., clear solution, suspension, dispersion) that is capable of treating, e.g., saturating, a backing so as to effectively apply LAB and/or elastomer to the backing when the solvent is removed.

Solvents suitable for use in the present invention include any solvent that is able to effectively apply LAB and/or elastomer to an extendible backing. Preferably, the solvent will be able to saturate the backing and then be easily removed, e.g., by drying, in a manner that does not adversely effect the resultant tape. For reasons including their cost and their suitability for use with current manufacturing techniques ahd equipment (such as drying equipment), LAB's and elastomers that are soluble in organic solvents, as opposed to water, are generally preferred.

Examples of suitable solvents include water, and organic solvents such as xylene, toluene and methyl ethyl ketone, and appropriate combinations thereof. A preferred solvent, when using the preferred polyvinyl carbamate LAB, is toluene.

Pressure-sensitive adhesives can be any of a variety of materials known for such uses, and are generally applied by, means well known to those skilled in the art as coatings, e.g., laminates, to the skin-facing side of th,e backing. Such adhesives are typically "hypoallergenic" in that they exhibit acceptable performance in the 21-day Draize test on human subjects. Pressure-sensitive adhesives can be used with primers, tackifiers, plasticizers and other additiYes as will be known in the art. The adhesives are preferably sufficiently tacky in their normal dry state, and have a desired balance of adhesion, cohesion, stretchiness, elasticity and strength for medical use.

Examples of preferred adhesives are those described in U.S. Pat. No. RE 24,906, particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 which comprise block copolymers having three or more polymer block structures having a general configuration —A—B—A— wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are iso-octyl acrylate/n-vinyl pyrrolidone copolymer adhesives and crosslinked acrylate adhesives such as for example those described in U.S. Pat. No. 4,112,213.

DESCRIPTION OF THE DRAWINGS

Referring now to the drawing, there is shown in FIG. 1 a diagram of a preferred method of making tape material of the present invention. The equipment is of a type commonly used in the processing of fabrics such as non-woven webs. As is readily apparent to one skilled in the art, other equipment and procedures than those illustrated may be used without departing from the scope of the invention.

A fabric backing (10) ("Sontara 8010") is led from supply roll (12) to between pressure rolls (14) and (16) where it is laminated on its rougher side under very low pressure with an incoming coating (18) of pressure-sensitive adhesive that had been previously cast by pressure feed die (20) on a carrier web (22) of silicone-surfaced release liner (20) ( "1-60 Bkg-157", Daubert, Oak Brook, Ill.) that had been led off supply roll (24). The coating (18) had been partially dried in ovens (21) to a concentration of 65–90% solids. The combined webs (26) are led to a set of nip rolls (28) and (30) having a pre-set gap. The lower nip roll (30) dips into a trough (32) containing a 1:2 solution (34) (7.5% total solids) of an LAB (polyvinyl carbamate, 5% in toluene) and an elastomer ("Kraton 1101", 10% in toluene), and transfers this solution to the passing web (26). The wet web (36) is then passed through an air drying oven (38) wherein the solvent is evaporated by heating in two stages, i.e., at 80° C., then 116° C., for a total of 3-5 minutes. The dried tape material (40) is then separated from release liner (22) and is wound up on a roll (42). Release liner is then wound onto take-up rolls (43).

The tape material (40) can be used in various forms known in the art. Preferably the tape material is converted, e.g., cut and assembled in the form of a roll or in the form of a tape pad as described in (co-pending U.S. patent application Ser. No. 732,587), the disclosure of which is hereby incorporated by reference.

In FIG. 2 is shown a sectional view of a portion of a preferred tape (40) having a fabric backing (10). The face side (46) of the backing is coated with a pressure-sensitive adhesive (18). The fabric backing (10) itself contains both an LAB and an elastomeric coating that impart both release characteristics and elasticity to the backside (44) of the tape, without adversely affecting the moisture vapor permeability, softness or conformability of the tape. As a result, the tape can be wound in a linerless roll or made into a tape pad, and when needed, can be easily removed from the roll or pad and used without deformation of the backing or substantial loss of adhesion.

FIG. 3 shows a side elevational view of a roll (48) of tape (40) of the present invention that has been wound directly upon itself. On its face side (46) the tape has a tacky pressure-sensitive adhesive (18). On its backside (44) the tape has been coated in a one-pass coating operation with a compatible combination of LAB and elastomer. In roll form, the backing serves as a permanent support for the adhesive coating as well as a temporary liner, in that each concentric turn of the roll temporarily and removably contacts and covers the adhesive surface of the overlying turn.

The limited adhesion between the backing and the adhesive keeps the roll in its wound form, yet makes it possible to unwind the tape without deformation of the backing or substantial loss of adhesion.

In FIG. 4 is shown an enlarged elevational view of a preferred tape pad (50) for dispensing tape material, wherein a plurality of individual sheets (52) of tape (40) of the invention each having a backside (44) and a faceside (46) are superimposed on one another and attached to a base support (58) at the bottom-most sheet. Also included at peripheral edge (54) on the faceside (46) on each sheet (52) is a liner strip (56) for facilitating manual separation of the sheets. The liner strip is then easily removed so that the entire adhesive coating on the sheet will be adhered to the skin.

EXAMPLES

The following examples are given to illustrate, but not limit, the scope of the invention. Unless otherwise indicated, all parts and percentages are by weight.

EXAMPLE 1

Samples were prepared by conventional hand-lamination techniques in order to compare the effect of the one-pass coating operation of the present invention with a traditional two-pass coating operation, for the application of elastomer and LAB to a suitable fabric backing. These samples were compared to untreated fabric backing and fabric backing treated in a similar manner with either elastomer or LAB alone.

A layer of an iso-octyl acrylate/n-vinyl pyrrolidine adhesive was prepared as described in U.S. Pat. No. 4,112,213 and coated on a sheet of silicone release liner ("1-60 Bkg-157", Daubert Co., Oak Brook, Ill.) at a thickness (8 mil) calculated to yield a dry adhesive weight of 0.71 g per 20×50 cm sample square. The adhesive layer was then partially air-dried to a concentration of between 65 and 90% solids.

Pieces of fabric backing ("Sontara 8010"), 20×50 cm in size were placed onto the partially dried adhesive layer and pressed in place by hand. The backing pieces were then placed in an oven at (99° C.) for 7 minutes, at which time they were removed and hand-laminated by a conventional technique, i.e., applying 200 g/cm without heat, by means of a 12 volt, 30.5 cm variable laminator ("Laminex", Rexham Co., Matthews, N.C.).

Samples of the resultant laminates were either left untreated or were saturated with either LAB alone (5% solids) or elastomer alone (10% solids) in a manner analogous to that described below.

One group of samples of the laminates were saturated with a 1:2 solution of LAB (polyvinylcarbamate, 5% solids in xylene-toluene, 22:78) and elastomer ("Kraton 1101", 10% solids in toluene) for a total solids concentration of 7.5%. The excess solution was drained off and the resultant treated fabric was dried in an air oven at 104° C. for 7-10 minutes, until no further solvent could be detected by smell.

Another group of laminates were saturated first with a 5% solids solution of "Kraton 1101" in toluene. The excess solution was drained off and the treated fabric was dried in an air oven at 104° C. for 7-10 minutes. The dried, elastomer-containing fabric was then saturated with a 2.5% solids solution of polyvinylcarbamate in xylene- toluene (22:78). The excess was again drained off and the sample similarly dried.

TABLE 1 sets forth the results of evaluations of the above described fabrics. The absolute figures are not critical, rather the values can be best compared, in relative terms, with samples similarly prepared and evaluated.

The first group (columns A through C) sets forth the various physical characteristics of the samples including:

(A) the ratio of LAB to elastomer in the saturating solution;

(B) the percent of total solids in the saturating solution; and

TABLE 1

| Sample | A LAB elastomer | B Total % solids | C saturant % | D adh-steel $T_o$ | E adh-bkg $T_o$ | F adh-steel aft E | G adh-bkg $T_{24}$ | H adh-steel aft G | J MVT (g/m² -day) | K porosity (sec) | L stiffness (g) | M elongation (%) | N tensile (Kg) | O $F_{10\%}$ |
|---|---|---|---|---|---|---|---|---|---|---|---|---|---|---|
| Fabric | — | — | — | 436.6 | 878.9 | 229.7 | 1287.2 | 170.1 | 6134 | 0.9 | 13 | 169 | 2.84 | 0.04 |
| Fabric & LAB | 1:0 | 5 | 7.8 | 190.9 | 48.2 | 181.5 | 51.0 | 130.4 | 7347 | 1.54 | 94 | 142 | 3.73 | 0.49 |
| Fabric & elastomer | 0:1 | 10 | 9.0 | 272.2 | 96.4 | 226.8 | 187.1 | 181.5 | 4833 | 1.56 | 61 | 145 | 3.81 | 0.34 |
| Fabric & | 2:1 | 5,2.5 | 14.4 | 130.4 | 34.0 | 124.8 | 45.4 | 87.9 | 8312 | 1.66 | 66 | 144 | 4.49 | 0.45 |

TABLE 1-continued

| Sample | A LAB elastomer | B Total % solids | C saturant % | D adhsteel $T_o$ | E adhbkg $T_o$ | F adhsteel aft E | G adhbkg $T_{24}$ | H adhsteel aft G | J MVT (g/m$^2$-day) | K porosity (sec) | L stiffness (g) | M elongation (%) | N tensile (Kg) | O $F_{10\%}$ |
|---|---|---|---|---|---|---|---|---|---|---|---|---|---|---|
| elastomer, LAB (2-pass) | | | | | | | | | | | | | | |
| Fabric & LAB/ elastomer (1-pass) | 1:2 | 7.5 | 10.7 | 195.6 | 34.0 | 147.4 | 62.4 | 161.6 | 5379 | 1.59 | 57 | 151 | 3.80 | 0.50 |

(C) the percent weight of saturant incorporated.

The second group (columns D through H) sets forth adhesion determinations for each tape.

Adhesion was evaluated according to ASTM D-1000, using steel or backing material of the same type tape being tested and is expressed in grams. Samples were tested directly after adhesion ($T_O$) or at 24 hours after adhesion ($T_{24}$), in the cross-web direction using an Instron Model (Instron Corp., Canton, Mass.) or an "Intelect II", Thwing-Albert, Philadelphia, Pa.

The determinations include:

(D) adhesion to steel ($T_O$);
(E) adhesion to backing ($T_O$);
(F) adhesion to steel after (E);
(G) adhesion to backing ($T_{24}$); and
(H) adhesion to steel after (G).

The third group (columns J through N) includes evaluations of various properties of the final tape products, including:

(J) moisture vapor transmission, evaluated in a manner analogous to ASTM E96-80, and expressed in grams transmitted per square meter per day;
(K) porosity, evaluated by a procedure wherein the time (in seconds) necessary for an inner cylinder of a densometer to force 100 cc of air through a 25 mm circular sample of the fabric is determined, in a manner analogous to that described in ASTM D737-75;
(L) softness, evaluated by a procedure wherein the force (in grams) necessary to pull a 2.9 cm diameter piece of the fabric through a 1.9 cm aperture is determined, in a manner similar to that described in ASTM D4032-82;
(M) elongation, evaluated by ASTM Method No. D-1682-64 and expressed in percent elongation at failure;
(N) tensile, evaluated by Method No. D1682-64, and expressed in kilograms of force at failure; and
(O) $F_{10\%}$ modulus, evaluated by INDA Standard Test 90-75 (R77) and expressed as the force applied at 10% elongation, in kilograms.

The results in TABLE 1 indicate that the tape produced by a conventional two-pass operation is inferior for use as a medical tape. In contrast, the tape produced by a one-step operation according to the present invention performs exceptionally well in every respect as a medical tape.

In particular it can be seen that the tape produced by the two-pass operation is stiffer (e.g., softness values are greater), and exhibits poorer adhesion values, e.g., at column (14), which indicates that there is a greater tendency for loss of adhesion, caused presumeably by the transfer of LAB from a coating on the backing for the two-pass product to the adhesive surface.

Similarly, there is a tendency for more total solids to be deposited by a two-pass operation as opposed to the one-pass operation of the present invention, thereby increasing the cost associated with the two-pass operation in terms of materials, as well as time and effectiveness.

The tape produced by the one-step operation can be further used to prepare tape pads, as described in (U.S. patent application Ser. No. 732,587). Each sheet of the pad is removable without apparent deformation or substantial loss of adhesion.

EXAMPLE 2-5

The following TABLE 2 shows examples of tapes made by a one-pass operation of this invention. Unless otherwise indicated, Examples 3, 4, and 5b were prepared by hand as described in EXAMPLE 1, and the remaining Examples were prepared by machine as described with reference to FIG. 1.

TABLE 2

| Sample | A LAB elastomer | B Total % solids | C saturant % | D adhsteel $T_o$ | E adhbkg $T_o$ | F adhsteel aft E | G adhbkg $T_{24}$ | H adhsteel aft G | J MVT (g/m$^2$-day) | K porosity (sec) | L stiffness (g) | M elongation (%) | N tensile (Kg) | O $F_{10\%}$ |
|---|---|---|---|---|---|---|---|---|---|---|---|---|---|---|
| Example 2 | | | | | | | | | | | | | | |
| a | 1:2 | 7.5 | 10.0 | 275.0 | 99.2 | 255.2 | 136.1 | 147.4 | 8295 | 0.2 | 56 | 155 | 3.86 | 0.41 |
| b | 1:2 | 7.5 | 12.1 | 255.2 | 93.6 | 192.8 | 104.9 | 133.2 | 7311 | 0.3 | — | 162 | 3.90 | 0.32 |
| c | 1:2 | 7.5 | 10.7 | 269.4 | 79.4 | 241.0 | 87.9 | 170.1 | 8266 | 0.1 | — | 103 | 4.22 | 0.23 |
| Example 3 | | | | | | | | | | | | | | |
| a | 1:1 | 5.0 | 6.2 | 178.6 | 34.0 | 164.4 | 34.0 | 130.4 | 3544 | 1.5 | 81 | 175 | 3.72 | 0.54 |
| b | 1:2 | 7.5 | 9.04 | 147.4 | 22.7 | 155.9 | 34.0 | 130.4 | 3070 | 5.2 | 78 | 150 | 3.95 | 0.64 |
| c | 1:3 | 10.0 | 12.27 | 184.3 | 25.5 | 155.9 | 28.4 | 121.9 | 2769 | 13.6 | 89 | 148 | 4.08 | 0.64 |
| d | 1:4 | 12.5 | 19.37 | 178.6 | 28.4 | 187.1 | 31.2 | 124.8 | 1934 | 15.7 | 107 | 143 | 4.49 | 0.73 |
| Example 4 | | | | | | | | | | | | | | |
| a | 9:1 | 7.5 | 12.7 | 164.4 | 25.5 | 138.9 | 42.5 | 116.2 | 3739 | 2.2 | 117 | 125 | 4.13 | 0.95 |
| b | 4.7:1 | 7.5 | 11.6 | 195.6 | 25.5 | 170.1 | 48.2 | 127.6 | 2972 | 3.0 | 99 | 125 | 3.81 | 0.91 |
| c | 3:1 | 7.5 | 13.3 | 192.8 | 25.5 | 153.1 | 51.0 | 133.2 | 3664 | 3.1 | 108 | 120 | 3.90 | 0.86 |
| d | 2:1 | 7.5 | 16.9 | 170.1 | 25.5 | 153.1 | 51.0 | 113.4 | 3265 | 2.8 | 108 | 130 | 4.22 | 0.95 |
| e | 1:1 | 7.5 | 13.3 | 164.4 | 22.7 | 161.6 | 39.7 | 127.6 | 3483 | 3.7 | 111 | 147 | 4.31 | 0.86 |
| f | 1:2 | 7.5 | 14.9 | 184.3 | 28.4 | 164.4 | 39.7 | 136.1 | 3830 | 2.5 | 101 | 147 | 4.35 | 0.73 |
| g | 1:4.7 | 7.5 | 9.9 | 192.8 | 42.5 | 173.0 | 34.0 | 136.1 | 3461 | 3.4 | 71 | 152 | 4.04 | 0.54 |

TABLE 2-continued

| Sample | A<br>LAB elastomer | B<br>Total % solids | C<br>saturant % | D<br>adh-steel $T_o$ | E<br>adh-bkg $T_o$ | F<br>adh-steel aft E | G<br>adh-bkg $T_{24}$ | H<br>adh-steel aft G | J<br>MVT (g/m$^2$-day) | K<br>porosity (sec) | L<br>stiffness (g) | M<br>elongation (%) | N<br>tensile (Kg) | O<br>$F_{10\%}$ |
|---|---|---|---|---|---|---|---|---|---|---|---|---|---|---|
| h | 1:9 | 7.5 | 11.6 | 178.6 | 42.5 | 170.1 | 53.9 | 119.1 | 3250 | 2.9 | 63 | 147 | 4.26 | 0.54 |
| Example 5 | | | | | | | | | | | | | | |
| a | 1:1 | 5.0 | 12.1 | 425.3 | 70. | 297.7 | 141.8 | 283.5 | 3196 | 0.4 | — | 28 | 7.53 | 1.81 |
| b | 1:2 | 7.5 | 2.8 | 433.8 | 48.2 | 382.8 | 133.3 | 232.5 | 925 | — | 120 | 28 | 10.39 | 8.07 |
| c | 1:1 | 5.0 | 12.2 | 226.8 | 65.2 | 155.9 | 99.2 | 155.9 | 5645 | 3.4 | — | 56 | 5.67 | 0.54 |

The same evaluations as were made in EXAMPLE 1 are listed for each tape.

The absolute figures are not critical in that different properties (e.g., adhesion, MVT, stiffness and the like) may be desired for different tasks. Nevertheless, the data indicates that a variety of concentrations and conditions as well as backings, LAB materials and elastomers can be used in the one-pass operation of the invention.

EXAMPLE 2 shows the effect of varying adhesive weights with a preferred tape produced according to this invention. As can be seen, each tape shows acceptable performance at each adhesive weight evaluated.

EXAMPLE 3 shows the properties of backings treated with varying ratios of preferred LAB and elastomer at varying percent total solids. As can be seen, release characteristics improve, e.g., adhesion to backing values go down with increasing solids content, but at the expense of MVT, stiffness and porosity.

An optimal level for this particular combination of ingredients therefore appears to be at a total solids level of about 10%.

EXAMPLE 4 shows the effect of varying the ratio of LAB to elastomer, keeping the total solids content of the saturant constant. Clearly at increasing proportions of elastomer the elasticity (e.g., elongation) of the fabric increases, while at increasing proportions of LAB release characteristics (e.g., adhesion to backing) improve. While every ratio evaluated provides a suitable tape, i.e., from 1:9 to 9:1 LAB:elastomer, an optional ratio of this particular LAB and elastomer appears to be about 1:1.

EXAMPLE 5 shows use of the following fabrics as backing for tapes prepared according to this invention. As can be seen each tape listed showed acceptable performance and in particular each benefited both in terms of elasticity and release characteristics from the one-pass treatment of LAB and elastomer.

a. unbranded stitch
b. "Durapore", Burlington
c. acetate tricot warpknit, Gold Mills, Inc.

What is claimed is:

1. A dispensable tape comprising a fibrous extensible backing, having a faceside and a backside, the faceside having been coated with a pressure-sensitive adhesive and the backside having been treated with at least one low adhesion backsize material and at least one elastomer, such that said low adhesion backsize material is present in a homogeneous and continuous form throughout said backing.

2. A dispensable tape comprising a fibrous backing having a faceside and a backside, the faceside having been coated with a pressure-sensitive adhesive and the backside having been treated simultaneously with a solution comprising
   (a) at least one low adhesion backsize material, and
   (b) at least one elastomer.

3. A dispensable tape according to claim 2 wherein the backing is selected from the group consisting of non-woven, woven and knitted fabrics comprising fibers selected from the group consisting of synthetic fibers, natural fibers, or blends thereof.

4. A dispensable tape according to claim 2 wherein the backing is a spun-laced polyester non-woven fabric.

5. A dispensable tape according to claim 2 wherein the low adhesion backsize material is selected from the group consisting of polyvinyl carbamate and derivatives thereof.

6. A dispensable tape according to claim 5 wherein the low adhesion backsize material is polyvinyl N-octadecyl carbamate.

7. A dispensable tape according to claim 2 the elastomer is selected from the group consisting of thermoplastic rubbers, vinyl chloride-vinyl acetate resins, acrylic resins, thermoplastic hydrocarbon resins, and modified aromatic urethane resins.

8. A tape roll comprising concentric overlying turns of a tape comprising a fibrous extensible backing having a faceside and a backside, the faceside having been coated with a pressure-sensitive adhesive and the backside having been treated simultaneously with a solution comprising
   (a) at least one low adhesion backsize material, and
   (b) at least one elastomer.

9. A tape pad sing a plurality of sheets, each sheet comprising a fibrous extensible backing having a faceside and a backside, the faceside having been treated with a pressure-sensitive adhesive and the backside having been treated simultaneously with a solution comprising
   (a) at least one low adhesion backsize compound, and
   (b) at least one elastomer.

10. A method of making dispensable tape comprising the steps of
   (a) treating a fibrous, extensible backing simultaneously with a solution comprising
      (i) at least one low adhesion backsize material, and
      (ii) at least one elastomer, and
   (b) drying the resultant treated backing to remove substantially all solvent,
wherein the backing is selected from the group consisting of non-woven, woven and knitted fabrics comprising fibers selected from the gorup consisting of synthetic fibers, natural fibers, or blends thereof.

11. A method of making dispensable tape comprising the steps of
   (a) treating a fibrous extensible backing simultaneously with a solution comprising
      (i) at least one low adhesion backsize material, and
      (ii) at least one elastomer, and
   (b) drying the resultant treated backing to remove substantially all solvent.

12. A method according to claim 11 wherien the backing is selected from the group consisting of nonwoven, woven and knitted fabrics comprising fibers selected from the group consisting of synthetic fibers, natural fibers, or blends thereof.

13. A method according to claim 11 wherein the backing is a spun-laced polyester non-woven fabric.

14. A method according to claim 11 wherein the low adhesion backsize material is selected from the group consisting of polyvinyl carbamate and derivatives thereof.

15. A method according to claim 14 wherein the low adhesion backsize material is polyvinyl N-octadecyl carbamate.

16. A method according to claim 11 wherein the elastomer is selected from the group consisting of thermoplastic rubbers, vinyl chloride-vinyl acetate resins, acrylic resins, thermoplastic hydrocarbon resins, and modified aromatic urethane resins.

17. A method according to claim 16 wherein the elastomer is a thermoplastic rubber.

* * * * *

UNITED STATES PATENT AND TRADEMARK OFFICE
CERTIFICATE OF CORRECTION

PATENT NO. : 4,967,740

DATED : November 6, 1990

INVENTOR(S) : John E. Riedel

It is certified that error appears in the above-identified patent and that said Letters Patent is hereby corrected as shown below:

Col. 2, line 14, "chosen" should read --chosen,--.

Col. 2, line 47, "teristics" should read --characteristics--.

Col. 5, line 67, "extendible" should read --extensible--.

Col. 6, line 4, "ahd" should read --and--.

Col. 6, line 11, "A-preferred" should read --A preferred--.

Col. 6, line 15, "by, means" should read --by means--.

Col. 6, line 16, "th,e" should read --the--.

Col. 6, line 21, "additiYes" should read --additives--.

Col. 9, line 20, "Instron Model" should read
            --Instron Model 1130--.

Col. 11, line 62, "fibrous backing" should read
            --fibrous, extensible backing--.

Col. 12, line 26, "claim 2 the" should read
            --claim 2 wherein the--.

Col. 12, line 32, "fibrous extensible" should read
            --fibrous, extensible--.

UNITED STATES PATENT AND TRADEMARK OFFICE
CERTIFICATE OF CORRECTION

PATENT NO. : 4,967,740

DATED : November 6, 1990

INVENTOR(S) : John E. Riedel

It is certified that error appears in the above-identified patent and that said Letters Patent is hereby corrected as shown below:

Col. 12, line 61, "fibrous extensible" should read --fibrous, extensible--.

Col. 12, line 67, "wherien" should read --wherein--.

Signed and Sealed this

Twenty-fifth Day of May, 1993

Attest:

MICHAEL K. KIRK

*Attesting Officer*  Acting Commissioner of Patents and Trademarks